United States Patent
McColl et al.

(10) Patent No.: US 6,488,717 B1
(45) Date of Patent: Dec. 3, 2002

(54) PROSTHETIC LEG

(76) Inventors: Mack Edward McColl, 16728 - 113 Ave., Edmonton, AB (CA), T5M 2X3; Colin Clegg, 16728 - 113 Ave., Edmonton, AB (CA), T5M 2X3

(*) Notice: Subject to any disclaimer, the term of this patent is extended or adjusted under 35 U.S.C. 154(b) by 0 days.

(21) Appl. No.: 09/682,370

(22) Filed: Aug. 24, 2001

(51) Int. Cl.$^7$ .................................................. A61F 2/80
(52) U.S. Cl. ...................................................... 623/35
(58) Field of Search .............................. 623/35, 38, 27, 623/28, 29, 30, 31, 32, 33, 34, 36

(56) References Cited

U.S. PATENT DOCUMENTS

| | | | |
|---|---|---|---|
| 2,657,393 A | 11/1953 | Haller | |
| 3,707,731 A | * 1/1973 | Morgan | 623/38 |
| 4,038,705 A | 8/1977 | Owens et al. | |
| 4,051,558 A | 10/1977 | Vallotton | |
| 4,215,441 A | 8/1980 | Wilson | |
| 4,370,761 A | 2/1983 | Serri | |
| 4,619,660 A | 10/1986 | Christiansen et al. | |
| 4,883,493 A | 11/1989 | Martel et al. | |
| 4,938,775 A | * 7/1990 | Morgan | 623/27 |
| 5,702,488 A | 12/1997 | Wood et al. | |
| 5,720,474 A | 2/1998 | Sugiyama | |
| 5,800,562 A | 9/1998 | Wilkinson | |
| 5,888,214 A | 3/1999 | Ochon | |
| 5,961,556 A | 10/1999 | Thorn | |
| 5,984,972 A | 11/1999 | Huston et al. | |
| 6,080,197 A | 7/2000 | Chen | |
| 6,086,615 A | 7/2000 | Wood et al. | |
| 6,214,056 B1 | 4/2001 | Wilkinson | |

FOREIGN PATENT DOCUMENTS

| | | |
|---|---|---|
| CA | 2253631 | 11/1998 |
| CA | 2276369 | 6/1999 |
| CA | 2291629 | 11/1999 |
| CA | 2321591 | 8/2000 |
| EP | 1099431 A1 | 9/2000 |

* cited by examiner

*Primary Examiner*—David H. Willse
*Assistant Examiner*—William H. Matthews
(74) *Attorney, Agent, or Firm*—Bennett Jones LLP

(57) ABSTRACT

A jointless leg prosthesis includes a reciprocating pylon and a coil spring. A pin affixes a lower flange fitting to one pylon member which passes through a slot formed in the other pylon member and an low-friction insert within the other pylon member. At the bottom end, the pylon terminates in an adapter which rotates freely within a heel pedestal. At the top end, the pylon attaches to a stump socket by conventional means.

13 Claims, 2 Drawing Sheets

PROSTHETIC LEG

BACKGROUND OF INVENTION

The present invention relates to a prosthetic leg.

Leg prostheses are designed to enable disabled persons to have a reasonable amount of mobility and activity. The simplest leg prosthesis is a peg leg, which enables a person to walk. Advances in the design of prosthetic legs attempt to mimic the biomechanics of those portions of the leg that are missing. Depending on the amputee's circumstances, however, walking and sitting motions may be all that can be supplied in the prior art mechanics of prosthetic legs, especially with persons having above the knee (AK) amputations.

U.S. Pat. No. 4,883,493 issued to Martel et al. describes a prosthesis including a knee joint, a telescoping and resilient shank and a rigid foot prosthesis. Many other prosthetic designs incorporate a shock-absorbing design using sprints, elastomeric elements or compressible fluid elements. Most such designs are unsatisfactory because force dampening purposely inhibits the return of energy that stimulates normal walking momentum. Therefore, most shock absorbing designs do not function well. As well, prior art designs to include shock absorption are complex, increasing the weight and cost of the prosthesis, both of which are negative factors.

Prior art prostheses generally include a prosthetic foot that attempts to mimic the function of a human foot and ankle joint. Simpler foot prostheses include a bent resilient member which flexes somewhat. However, it is known that when pushing off in a walking motion, a foot becomes very rigid, therefore, a flexible artificial foot hinders normal walking motion. Complicated artificial ankles and feet have been devised, such as that disclosed in U.S. Pat. No. 2,657,393. However, such complicated designs are difficult to maintain and very costly.

It is also beneficial to allow some rotational movement between stump and heel strike. In natural walking gaits, there is considerable rotation in the heel, especially in relation to the hip. In U.S. Pat. No. 4,038,705 issued to Owens et al., a thrust bearing assembly is provided which allows limited rotational movement. However, the thrust bearing and a paddle element requires specially shaped elastomeric torque members to restrain over-rotation, which is perceived as being problematic in the prior art.

Therefore, there is a need in the art for a leg prosthesis that provides functionality in a biomechanically safe and sound manner, which is also simple and inexpensive in design and construction.

SUMMARY OF INVENTION

The present invention is directed to a jointless leg prosthesis having an axially reciprocating pylon and a rotational heel. The prosthesis is exceedingly simple and efficient in design, yet functions well in both walking and running movements. In one embodiment, the entire prosthesis comprises only 18 parts, which compares favourably against the complex and costly prior art designs.

Accordingly, in one aspect, the invention comprises a leg prosthesis for use by a leg amputee comprising: (a) a reciprocating pylon comprising first and second concentric pylons, where said first pylon comprises an insert fitted within the first pylon, wherein the first pylon and insert define a slot accommodating a pin affixed to the second pylon, and said first pylon closely fits and slides within the second concentric pylon to permit axial displacement between the first and second pylon; (b) an outer flange fitting affixed to the first pylon and having a inward facing cup; (c) an opposite flange fitting affixed to the second pylon and having an inward facing cup; (d) a coil spring extending between and fitting within the opposite facing cups; (e) a pedestal having a lower ground-engaging surface that supplies 360 degree rotation at heel strike, and an upper surface defining a cylindrical opening; (f) an adapter affixed to the second pylon, said adapter having a lower circular disc fitting closely within the pedestal cylindrical opening; wherein the insert and adapter each comprise a low-friction material such that additional lubrication or seals are not required.

BRIEF DESCRIPTION OF DRAWINGS

The invention will now be described by way of an exemplary embodiment with reference to the accompanying simplified diagrammatic, not-to-scale drawings. In the drawings.

DETAILED DESCRIPTION

The present invention provides for a leg prosthesis. When describing the present invention, all terms not defined have their common art-recognized meanings.

Figure 1:
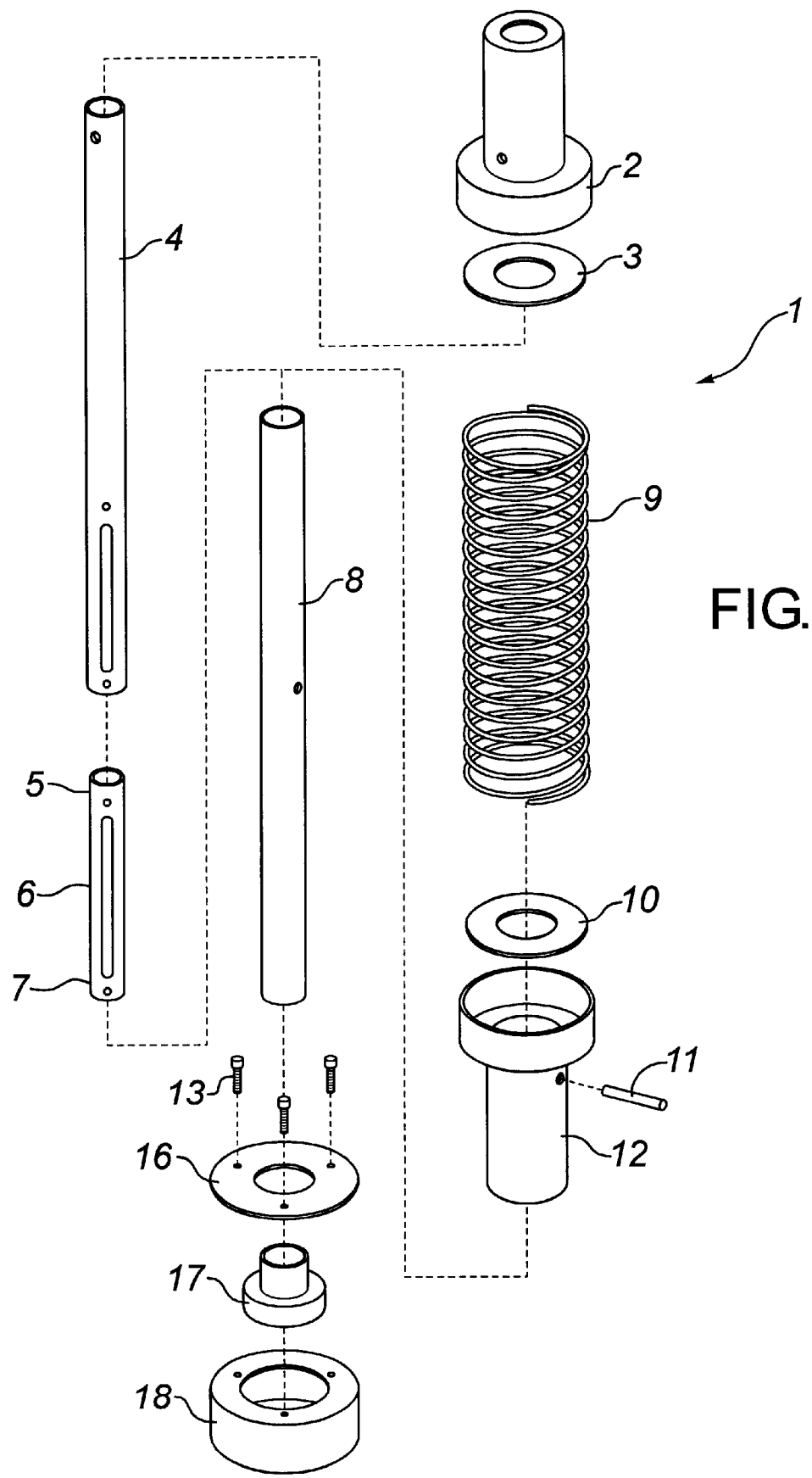
FIG. 1 is an exploded view of one embodiment of a leg prosthesis of the present invention.
Figure 2:
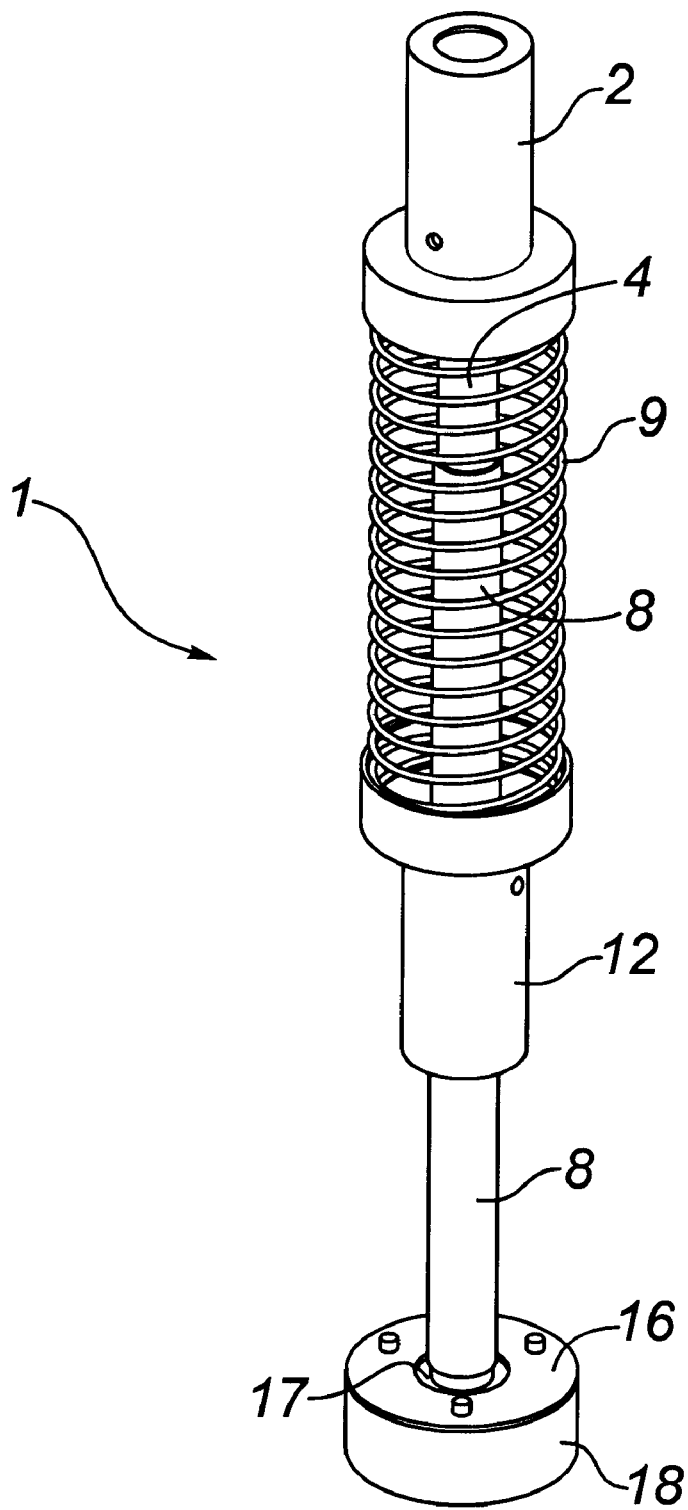
FIG. 2 is a pictorial view of an assembled leg prosthesis

The apparatus, as shown in FIGS. 1 and 2, comprises a reciprocating pylon which is formed from an inner pylon (4) and an outer pylon (8). The inner pylon (4) fits precisely within the outer pylon (8). The fit is not so tight as to frictionally prevent axial reciprocation of the inner pylon within the outer pylon, but is not so loose as to introduce significant non-axial movement of the inner pylon within the outer pylon. The inner and outer pylons (4, 8) may be fashioned from chromium-molybdenum steel, which provides high strength while minimizing weight. Materials such as carbon fibre composites or titanium may also be utilized.

In the embodiment illustrated by FIG. 2, the inner pylon (4) extends outside the outer pylon (8) and is affixed to a flange fitting (2) having an inside facing cup. The diameter of the cup is such that one end of the coil spring (9) will fit snugly within the flange cup. Similarly, the outer pylon (8) is affixed to an opposite flange fitting (12) approximately midway along the length of the outer pylon. The outside end of the coil spring (9) fits within and is retained by the flange fitting (12) and slot pin (11). In one embodiment, as shown in FIG. 1, low-friction washers (3,10) made-of a material such as nylon are placed in the cups of both flanges (2,12) to permit rotation of the coil spring (9) within the fittings, to further reduce wear on slot pin (11).

In one embodiment, the lower flange fitting (12) is affixed to the outer pylon (8) by means of the pin (11), which passes through the outer pylon and the slot portion of the inner pylon (4). A friction-reducing insert (6), fashioned from a material such as nylon, is fit within the tubular structure of the inner pylon. Accordingly, a slot is provided in both the inner pylon and the insert (6) to accommodate slot pin and permit the essential axial displacement of separate pylons.

The lower, outer pylon (8) forms half or more of the shank, and contains the pedestal-foot adapter (17) which is friction-fit or otherwise affixed into the end of the outer pylon (8). The adapter is preferably fashioned from a low-friction material such as nylon. The adapter (17) has a cylindrical base that fits precisely within the cylindrical opening on top of the pedestal (18) which is the ground-engaging portion of the prosthesis. The adapter (17) fits into the pedestal to provide heel-like rotational ability, completely free 360 degrees. Again, the fit of the adapter in the pedestal allows free rotation without any free play. The pedestal is retained to the adapter by a cap (16) affixed to the pedestal by screws or other fasteners.

The coil spring (9) is chosen with the body weight of the amputee in mind. The amount of axial movement during walking (or low activity) should preferably be about half the total axial movement afforded. The axial movement available may be about 8.5 cm or 3¾–4" for the adult size, and 4.5 cm for a smaller size, suitable for children. Therefore it is necessary that the spring strength exceed the body weight of the amputee by a factor greater than about 1.5 and approaching 2.0. In a normal walking motion, the prosthesis will contract less than halfway before immediate recoil, enough to stimulate the natural rolling motion of the hip, and foregoing the "snapping action" required to straighten a mechanical knee. When running, or negotiating all-terrain conditions, or stairs, significantly more force is placed on the prosthesis and more axial contraction ensues. Under running conditions, the spring delivers rapidly increasing recoil to return the prosthesis to full extension. The following table illustrates some examples of spring weights which may be used to effect the necessary recoil:

TABLE 1

| Body Weight | Spring Load |
|---|---|
| 50–125 lbs. | 200 lbs. |
| 125–200 lbs. | 250–500 lbs graduated |
| 200–250 lbs. | 500 lbs. |

For heavier individuals, it may be necessary to pre load the spring to accommodate extensive compression during normal walking. The spring load can be tailored specifically to the individual's actual weight and preference.

The coil spring is preferably fashioned from strong and lightweight metal such as chrome silica steel although other materials are not intended to be excluded from the scope of the invention. Suitable coil springs are commercially available, Other components may be fashioned from any suitable material. Aluminum and titanium alloys are preferred because of their light weight and high strength.

The top end of the prosthesis may attached to a conventional stump socket by conventional means. For AK amputees, the prosthesis is intended to be used without a knee joint, however, a locking (safety, or geriatric) knee may be employed, if desired, The total length of the prosthesis depends on whether it is intended for above knee amputee, hip disarticulated amputee, or below knee amputee. The length of the prosthesis may be modified by substituting inner and outer pylons of variable lengths, and employing axial movement of different amounts according to lengths of the stumps spring, and axial slot.

The bottom surface of the pedestal is preferably covered with a non-slip material such as rubber. An artificial foot may be attached to the pedestal for cosmetic purposes but should preferably be nonfunctional. Neither an prior art swing-phase knee nor an artificial foot should deflect, resist or aid flexion, as that is the function of the reciprocating pylon configuration. Therefore, the prosthetic leg operates jointless at the knee during walking and running functions, with 360 degree rotation at heel strike position.

As will be apparent to those skilled in the art, various modifications, adaptations and variations of the foregoing specific disclosure can be made without departing from the scope of the invention claimed herein.

What is claimed is:

1. A leg prosthesis for use by above-the-knee leg amputee comprising:
    (a) a reciprocating pylon comprising first and second concentric pylons, where said first pylon comprises an insert fitted within the first pylon, wherein the first pylon and insert define a slot accommodating a pin affixed to the second pylon, and said first pylon closely fits and slides within the second concentric pylon to permit axial displacement between the first and second pylon;
    (b) an outer flange fitting affixed to the first pylon and having a first inward facing cup;
    (c) an opposite flange fitting affixed to the second pylon and having a second inward facing cup;
    (d) a coil spring extending between and fitting within the first and second inward facing cups;
    (e) a pedestal having a lower ground-engaging surface that supplies 360 degree rotation at heel strike, and an upper surface defining a cylindrical opening;
    (f) an adapter affixed to the second pylon, said adapter having a lower circular disc fitting closely within the pedestal cylindrical opening; wherein the insert and adapter each comprise a low-friction material such that additional lubrication or seals are not required and wherein the prosthesis does not include an artificial knee joint.

2. The prosthesis of claim 1 wherein the pin affixes the opposite flange fitting to the second pylon.

3. The prosthesis of claim 1 wherein the insert and adapter comprise a plastic.

4. The prosthesis of claim 3 wherein the insert and adapter comprise nylon.

5. The prosthesis of claim 1 wherein the coil spring is chosen to have a strength greater than 150% of the body weight of the amputee.

6. The prosthesis of claim 5 wherein the coil spring has a strength greater than 175% of the body weight of the amputee.

7. The prosthesis of claim 6 wherein the coil spring has a strength greater than 200% of the body weight of the amputee.

8. The prosthesis of claim 1 wherein the reciprocating pylon permits axial displacement of about 4% to about 7% of the amputee's height.

9. A leg prosthesis consisting essentially of:
    (a) a reciprocating pylon comprising first and second concentric pylons, where said first pylon comprises an insert fitted within the first pylon, wherein the first pylon and insert define a slot accommodating a pin affixed to the second pylon, and said first pylon closely fits and slides within the second concentric pylon to permit axial displacement between the first and second pylon;
    (b) an outer flange fitting affixed to the first pylon and having an inward facing cup;
    (c) an opposite flange fitting affixed to the second pylon and having a second inward facing cup;
    (d) a coil spring extending between and fitting within the first and second inward facing cups;
    (e) a pedestal having a lower ground-engaging surface that supplies 360 degree rotation at heel strike, and an upper surface defining a cylindrical opening; (f) an adapter affixed to the second pylon, said adapter having a lower circular disc fitting closely within the pedestal cylindrical opening; and (g) a cap covering the pedestal and retaining the adapter within the pedestal; wherein said insert and adapter comprise a low-fiction material such that additional lubrication or seals are not required.

10. The prosthesis of claim 9 wherein the pin affixes the opposite flange fitting to the second pylon.

11. The leg prosthesis of claim 9 wherein the low-friction material comprises a plastic.

12. The leg prosthesis of claim 10 wherein the low-friction material comprises nylon.

13. The leg prosthesis of claim 9 wherein the entire prosthesis comprises 18 or fewer parts, including fasteners.

* * * * *